United States Patent [19]

Moriyama et al.

[11] Patent Number: 4,702,257

[45] Date of Patent: Oct. 27, 1987

[54] OPERATOR CONSOLE FOR IMAGING DIAGNOSTIC APPARATUS

[75] Inventors: Masao Moriyama; Masahiro Ohta; Toshiaki Yagi; Kazuhiro Kawano, all of Tokyo, Japan

[73] Assignees: Yokogawa Electric Corporation; Yokagawa Medical Systems, Limited, both of Tokyo, Japan

[21] Appl. No.: 911,734

[22] Filed: Sep. 26, 1986

[30] Foreign Application Priority Data

Nov. 25, 1985 [JP] Japan ............................ 60-264475

[51] Int. Cl.⁴ ............................................. A61B 5/05
[52] U.S. Cl. ..................................... 128/653; 378/4; 364/188
[58] Field of Search .................. 128/653, 659, 660; 324/309; 364/413–415, 188–190; 378/4, 20, 25, 26

[56] References Cited

U.S. PATENT DOCUMENTS

| | | | |
|---|---|---|---|
| 3,497,870 | 2/1970 | Balding | 364/190 |
| 3,720,817 | 3/1973 | Dinwiddie | 364/188 |
| 4,472,683 | 9/1984 | Sekihara et al. | 324/309 |
| 4,483,342 | 11/1984 | Pfeifer | 128/653 |
| 4,624,007 | 11/1986 | Muranushi | 378/20 |

Primary Examiner—William E. Kamm
Assistant Examiner—Ruth S. Smith
Attorney, Agent, or Firm—Moonray Kojima

[57] ABSTRACT

An operator console for use in an imaging diagnostic apparatus, comprising means for displaying a full length figure of a human body; means for displaying respective figures representing the axial plane, sagittal plane, and coronal plane of the body figure; means for displaying respective figures representing pitching, yawing, and rolling of these planes; plane designating means which are manipulated by an operator; and tilt direction designating means which are manipulated by an operator, whereby the plane and the tilt direction designated by the operator are displayed by means of the figures in connection with the body figure.

1 Claim, 16 Drawing Figures

FIG. 12(a)
Axial Plane

FIG. 12(b)
Sagittal Plane

FIG. 12(c)
Coronal Plane

OPERATOR CONSOLE FOR IMAGING DIAGNOSTIC APPARATUS

BACKGROUND OF THE INVENTION

1. Field of Invention

This invention relates to imaging diagnostic apparatus, such as CT (computerized tomography) apparatus and NMR (nuclear magnetic resonance) imaging apparatus; and more particularly, to an operator console for use in imaging diagnostic apparatus and which comprises mechanism for displaying intelligibly a scan plane of an object being examined.

2. Description of the Prior Art

Figure 10:
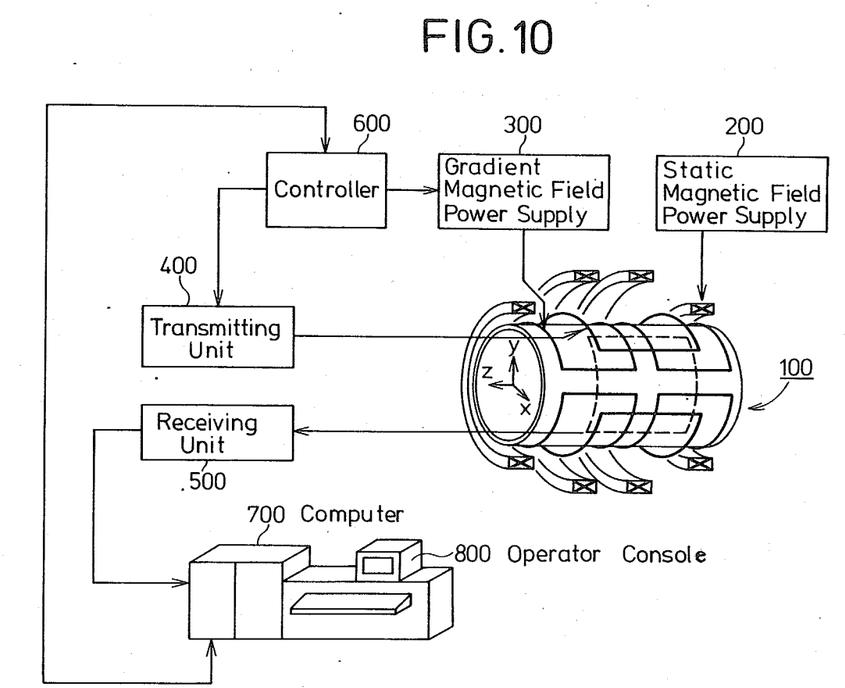
FIG. 10 is a schematic block diagram depicting an NMR imaging apparatus wherein the invention is used.

The NMR imaging apparatus and the CT apparatus are powerful tools for obtaining imaging diagnosis, in the field of clinical medicine and are currently in wide use. The NMR imaging apparatus comprises (for example, as shown in FIG. 10) a magnetic assembly 100 comprising static magnetic field coils (unnumbered) for producing a uniform static magnetic field and gradient magnetic field coils (unnumbered) for producing magnetic fields in the same direction as that of the static magnetic field and having linear gradients in the respective X,Y and Z directions; a static magnetic field power supply 200; a gradient magnetic field power supply 300; a transmitting unit 400 for supplying high frequency pulses (high frequency electromagnetic waves) to an object to be examined which is placed within the magnetic fields produced by magnetic assembly 100; a receiving unit 500 for receiving NMR signals coming from the object; a controller 600 for controlling the operation of transmitting unit 400 and magnetic assembly 100; a computer 700 for controlling controller 600, for processing received data, and for performing an image reconfiguration process over the section images of the object; and an operator console 800. Operator console 800 comprises a CRT for displaying an image and a control/display panel for setting a scan plane of the object at the time of data acquisition and displaying the scan plane thus set.

The scan plane of the object is set by means of three parameters, Plane, Tilt Direction, and Tilt Angle. These three parameters are used to display the spatial arrangment of the scan plane on the control/display panel, with respect to the object. Specifically, on the control/display panel are displayed the plane surface and the tilt direction by the use of letters and the tilt angle is displayed by use of a numerical value.

Figure 11:
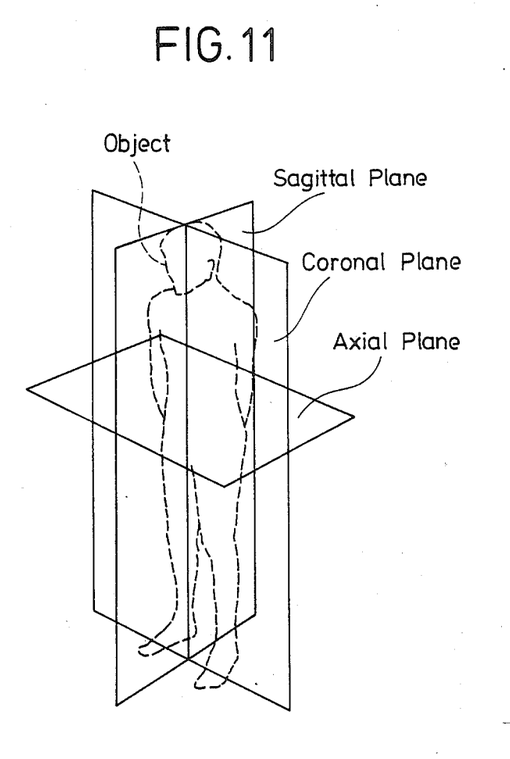
FIG. 11 is a pictorial view depicting scan planes.

The definitions of these three parameters are as follows:

PLANE. The plane is classified (as shown in FIG.11) into three mutually orthogonal reference surfaces imaged on the object, namely, (1) Sagittal plane, (2) Coronal plane, and (3) Axial plane.

Figure 12A:
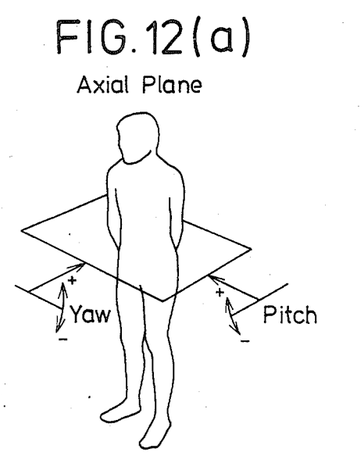
FIGS. 12(A), 12(B) and 12(C) are pictorial views depicting tilt directions of the scan plane.
Figure 12B:
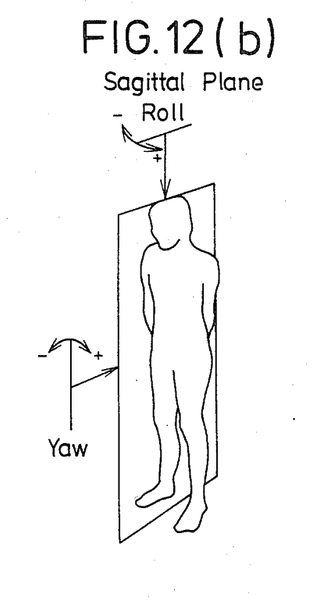
Figure 12C:
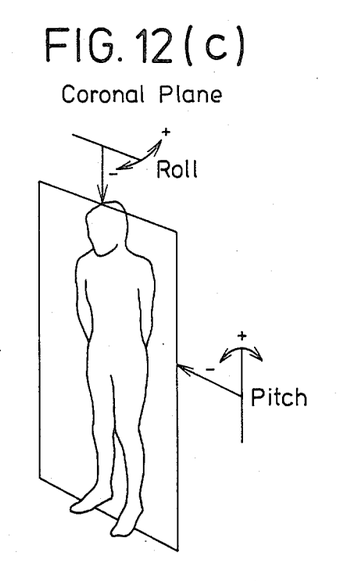

TILT DIRECTION The tilt direction is classified into three types, namely, (1) Pitching, (2) Yawing, and (3) Rolling. These terms indicate the inclination direction of each plane, as shown in FIGS. 12(A),12(B) and 12(C). More specifically, in FIG. 12(A), the tilt direction of the axial plane is indicated by Pitching and Yawing; in FIG. 12(B), the tilt direction of the Sagittal plane is indicated by Yawing and Rolling; and in FIG. 12(C), the tilt direction of the Coronal plane is indicated by Pitching and Rolling.

TILT ANGLE. The tilt angle is represented by "degree" which is indicative of the inclination angle of each plane.

These three parameters are used to indicate and display the scan planes, for example, in CT apparatus, and are widely used in the field of imaging diagnostic apparatus.

The conventional imaging diagnostic apparatus has an important deficiency, in that the conventional apparatus displays the spatial arrangement of the scan plane by use of letters and numerical characters and values. Thus, an operator must be relatively skilled to operate the conventional apparatus, and furthermore, such operator is prone to make various positioning and other errors, cause delays and in many ways increase the cost of diagnosis. The operator must perceive the three dimensional arrangement of the scan plane at the time of scanning or image decoding using only the letters and characters. Thus, the prior art leaves much to be desired in such diagnostic imaging devices.

SUMMARY OF THE INVENTION

Accordingly, an object of the invention is to overcome the aforementioned and other deficiencies and disadvantages of the prior art.

Another object is to provide an operator console for use in imaging diagnostic apparatus and which is equipped with display means for obtaining easy recognizability of the spatial arrangement of a scan plane with respect to an object being examined.

The foregoing and other objects are attained by the invention which encompasses an operator console comprising means for displaying a full length figure of a human body; means for displaying respective figures representing the axial plane, sagittal plane, and coronal plane of the body figure; means for displaying respective figures representing the pitching, yawing, and rolling of the planes; plane designating means which can be manipulated by the operator; and tilt direction designating means which can be manipulated by the operator, whereby the plane and tilt direction designated by the operator are displayed by means of figures in connection with the body figure.

DETAILED DESCRIPTION OF PREFERRED EMBODIMENTS

Figure 1:
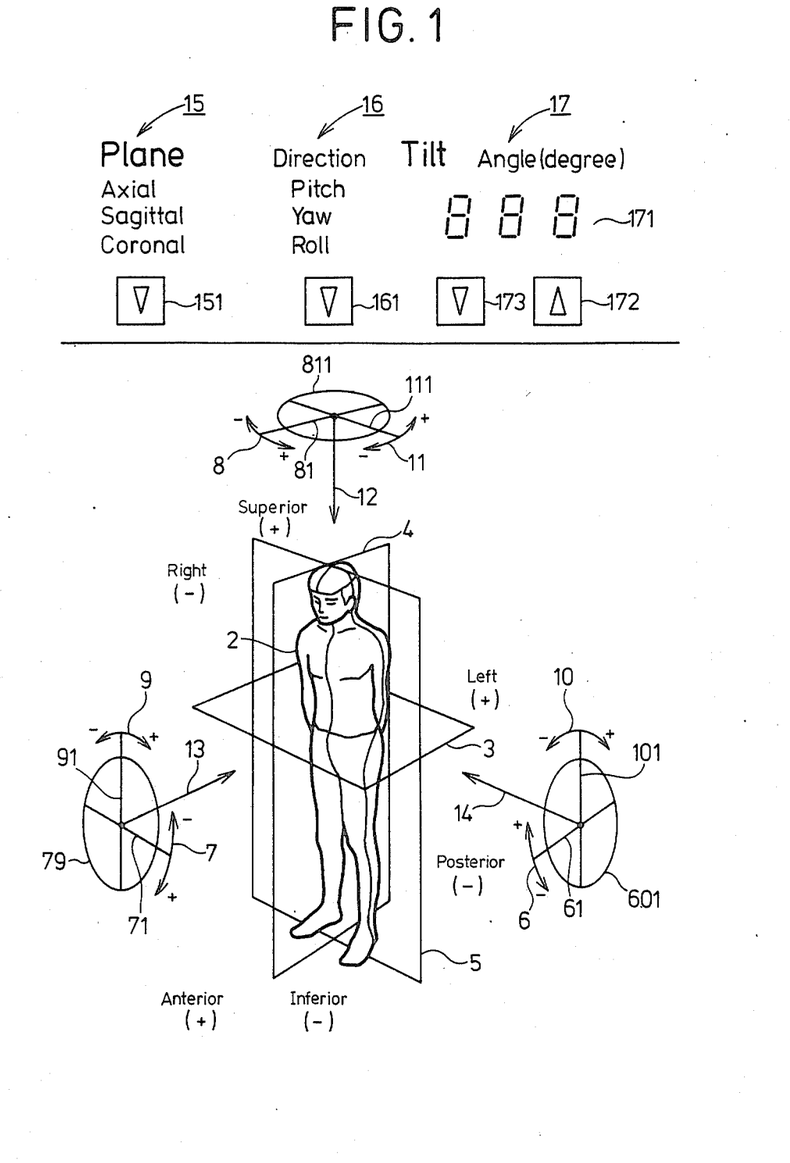
FIGS. 1,2,3 are configuration diagrams of an illustrative embodiment of the invention, showing the body figure and graphical lines indicating different parameters, the light emitting devices to illuminate the different parameters, and the system components to operate the arrangement.
Figure 2:
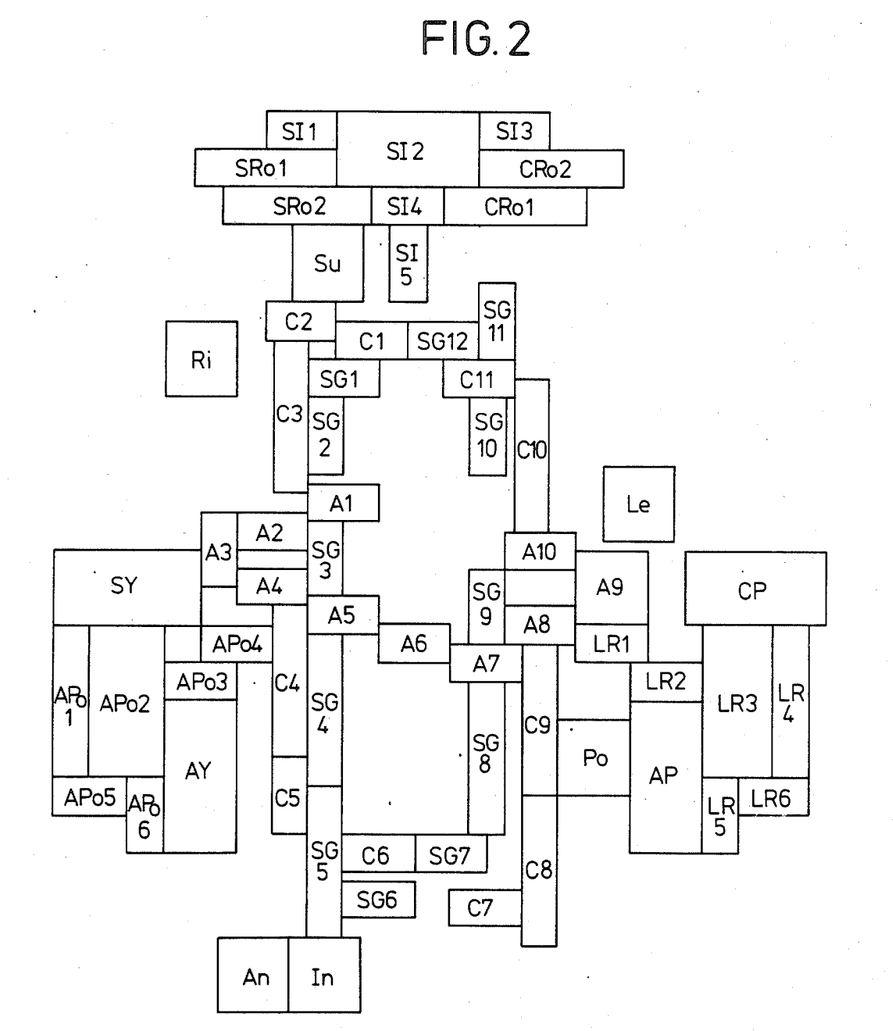
Figure 3:
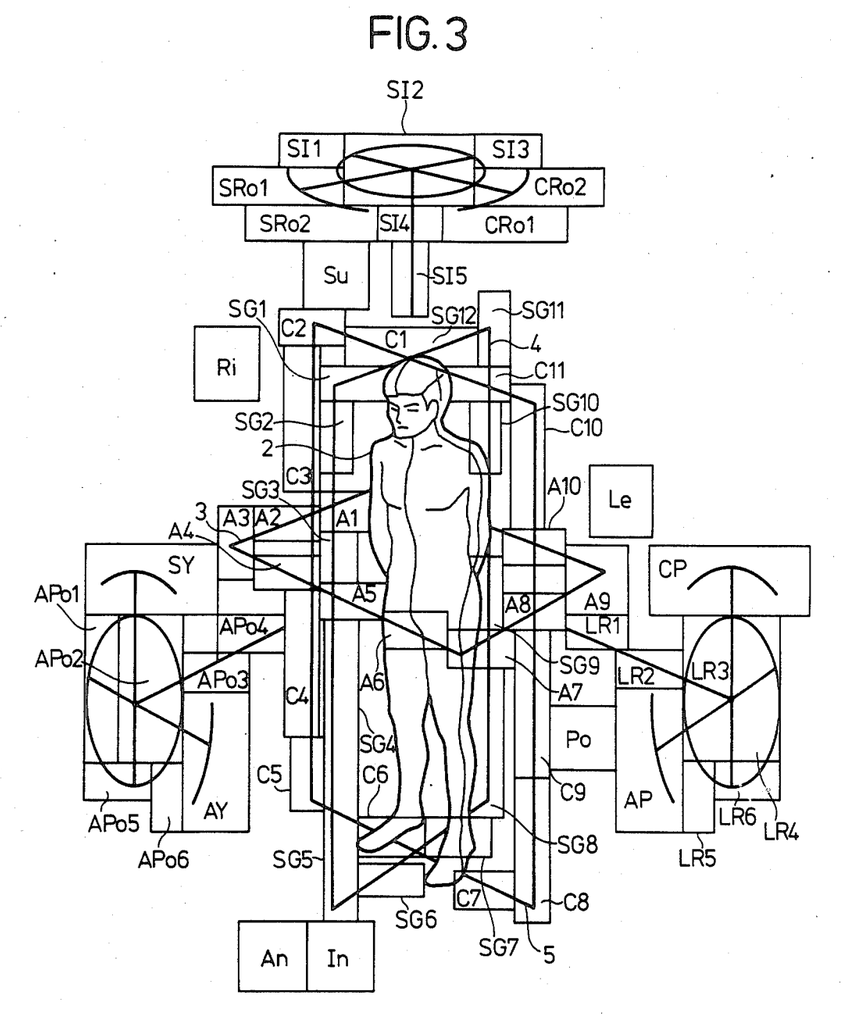

Turning now to FIGS. 1,2,3, FIG. 1 is a pictorial view depicting a control/display panel of the operator console. FIG. 2 is an arrangement diagram depicting a plurality of membrane light emitting elements (called herein "LED") for illuminating the control/display panel from its back side. FIG. 3 is a pictoral diagram depicting the relative positional relation between the figures depicted on the control/display panel and the LEDs. The membrane light emitting element LED comprises, for example, a combination of a light emitting diode and a translucent light dispersing member.

The control/display panel is made of an opaque sheet member. On the surface of the membrane is depicted a frontal full length FIG. 2 of a human body, as viewed obliquely from above. Frames 3,4 and 5 represent, respectively, the axial plane, the sagittal plane, and the coronal plane and are depicted by transparency lines and superposed on body FIG. 2. Similarly, arrows 6 and 7 represent Pitching and Yawing on the axial plane; arrows 8,9 represent Rolling and Yawing on the sagittal plane; and arrows 10 and 11 represent Pitching and Rolling on the coronal plane, and all are depicted by transparency lines.

Arrows 6,7 are depicted, respectively, at the points of transparency straight lines 61,71 which are parallel to two sides of frame 3 which represents the axial plane. Arrows 8,9 are depicted, respectively, at the points of transparency straight lines 81,91 which are parallel to the two sides of frame 4 which represents the sagittal plane. Arrows 10,11 are depicted, respectively, at the points of transparency straight lines 101,111 which are parallel to the two sides of frame 5 which represents the coronal plane. The straight lines 61,101 cross each other, and about this crossing point is depicted, by a transparency line, an ellipse 601. Similarly, straight lines 71 and 91 cross each other, straight lines 81 and 11 cross each other, and ellipses 79 and 811 are depicted in connection with these crossing straight lines. Ellipse 601 represents rotation of a plane caused by Pitching. Ellipse 79 represents rotation of a plane caused by Yawing. Ellipse 811 represents rotation of a plane caused by Rolling.

On the control/display device there are further depicted by transparent lines, the words "Superior (+) - Inferior (−)"; "Anterior (+) - Posterior (−)"; and "Left (+) - Right (−)", respectively, indicating the "upper - lower", the "front-rear" and the "left-right" of the body FIG. 2. Arrows 12,13,14 indicate the respective directions of Superior→Inferior; Anterior→Posterior; and Left→Right.

Above body FIG. 2, there are provided separately a Plane select/display section 15, a Tilt Direction select/display section 16, and a Tilt Angle control/display section 17. The Plane select/display section 15 comprises the title "Plane", transparency words "Axial", "Sagittal", and "Coronal", and a plane change over pushbutton 151. The Tilt Direction select/display section 16 comprises the title "Direction", transparency words "Pitch", "Yaw", and "Roll", and a tilt direction change over push button 161. The Tilt Angle select control/display section 17 comprises the title "Angle(degree)", a digital angle indicator 171, a tilt angle increment pushbutton 172, and a tilt angle decrement pushbutton 173.

In back of the transparency figures and letters are provided a plurality of LEDs distrubuted in such a manner as illustrated in in FIG. 2. Since the control/display panel is superposed on these LEDs, the relative positional relation shown in FIG. 3 is realized between body FIG. 2, plane representing frames 3,4,5, display words "Superior (+)-Inferior(−)", etc., and the individual LEDs. The correspondence of the figures on the side of the control/display panel to the individual LEDs is as follows:

| Symbols on Display Panel | Symbols of LEDs |
| --- | --- |
| Frame Axial 3 | $A_1$–$A_{10}$ |
| Frame Sagittal 4 | $SG_1$–$SG_{12}$ |
| Frame Coronal 5 | $C_1$–$C_{11}$ |
| Superior (+) | Su |
| Inferior (−) | In |
| Anterior (+) | An |
| Posterior (−) | Po |
| Left (+) | Le |
| Right (−) | Ri |
| SI Arrow 12 | $SI_1$–$SI_5$ |
| AP Arrow 13 | $APo_1$–$APo_6$ |
| LR Arrow 14 | $LR_1$–$LR_6$ |
| Ax. Pitch Arrow 6 | AP |
| Ax. Yaw Arrow 7 | AY |
| Sa. Yaw Arrow 9 | SY |
| Sa Roll Arrow 8 | $SRo_1$, $SRo_2$ |
| Co. Pitch Arrow 10 | CP |
| Co. Roll Arrow 11 | $CRo_1$, $CRo_2$ |

The LEDs $A_1$–$A_{10}$, $SG_1$–$SG_{12}$, and $C_1$–$C_{11}$ are energized by plane setting signals generated when the plane changeover pushbutton 151 is manipulated. The LEDs Le, Ri, Su, In, An, Po, $SI_1$–$SI_5$, $APo_1$–$APo_6$, $LR_1$–$LR_6$, AP, AY, SY, $SRo_1$, $SRo_2$, CP, $CRo_1$, and $CRo_2$ are energized by Tilt Direction setting signals generated when the Tilt Direction change over pushbutton 161 is manipulated.

The transparency words "Axial", "Sagittal", "Coronal" depicted the plane select/display section 15 and "Pitch", "Yaw", "Roll" depicted on the tilt direction select/display section 16 have respective membrane light emitting elements (not shown) provided in the rear thereof. Since these words are illuminated from their rear side, the plane and the tilt direction selected by the plane change over pushbutton 151 and the tilt direction change over pushbutton 161, are displayed immediately.

Figure 4:
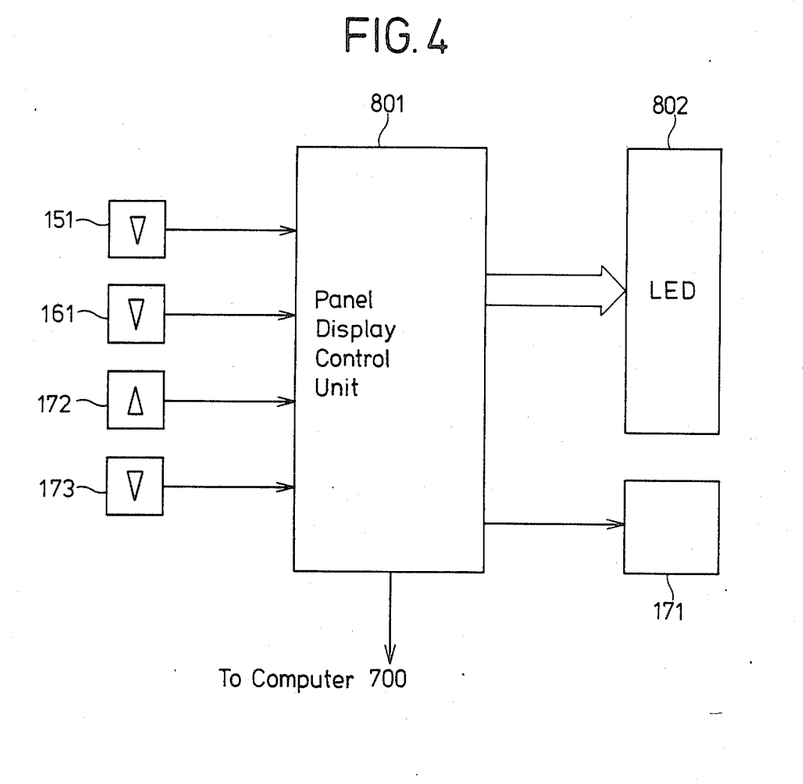
FIG. 4 is a block diagram depicting the illustrative embodiment.

The configuration of the operator console comprises the control/display panel as is shown in FIG. 4, wherein the output signals of a panel display control unit 801 applied with input signals from the plane change over pushbutton 151, tilt direction change over pushbutton 161, and tilt angle increment/decrement pushbuttons 172,173 become display control signals which are applied to an LED assembly 802 and tilt angle indicator 171. Panel display control unit 801 may be made, for example, of a microprocessor. A signal for designating the scan plane is applied from panel display control unit 801 to computer 700.

The operation of the embodiment will now be described with reference to FIGS. 5(A), 5(B) and 5(C).

OPERATION CAUSED BY PLANE CHANGE OVER PUSHBUTTON 151

Figures 5A, 5B, 5C:
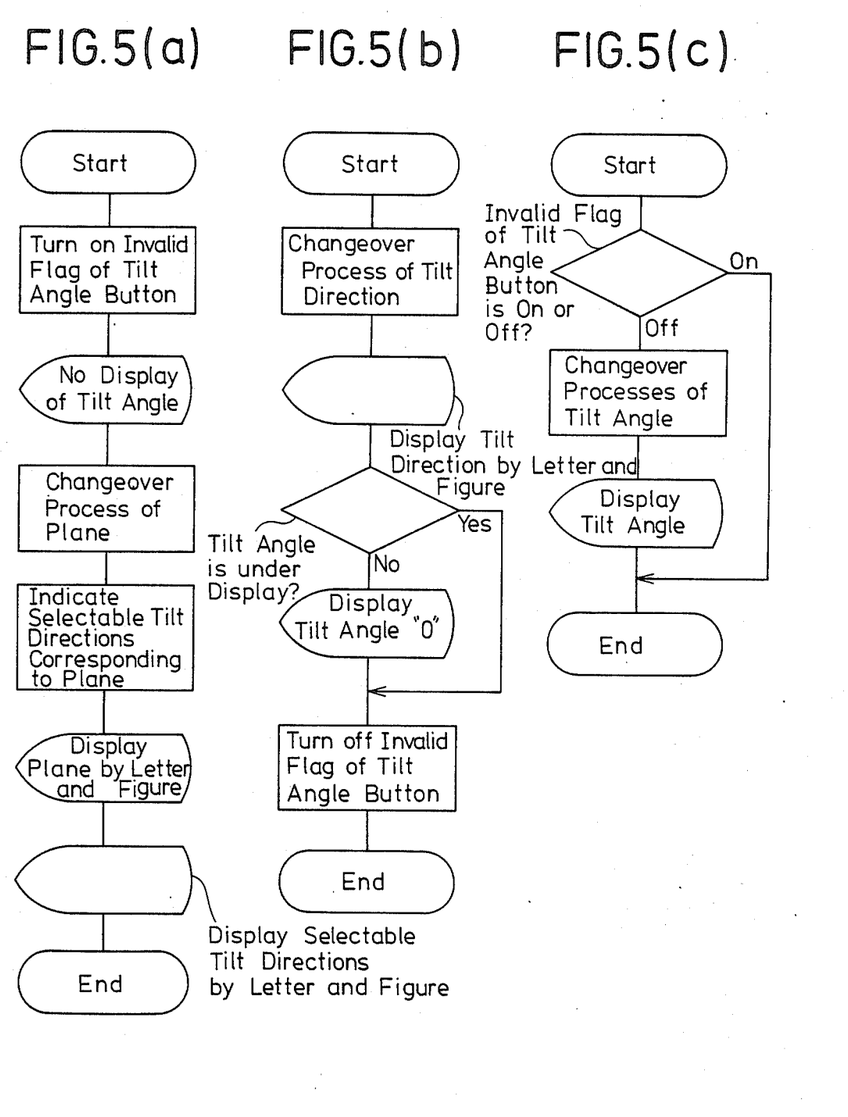
FIGS. 5(A), 5(B) and 5(C) are flow charts depicting the operation of the embodiment.

As shown in FIG. 5(A), as the plane change over pushbutton 151 is pushed, the individual planes are selected successively in the order of Axial plane, Sagittal plane, Coronal Plane, Axial Plane, etc, in response to each pushing. One plane is set when manipulation of the pushbutton is terminated. One frame corresponding to the thus set plane is made to illuminate and its plane name is displayed by means of illumination of the corresponding LED. Two selectable tilt directions, corresponding to the thus set plane, are displayed by means of figures and letters. At this time, the tilt angle is not displayed.

OPERATION CAUSED BY TILT DIRECTION CHANGE OVER PUSHBUTTON 161

As shown in FIG. 5(B), as the tilt direction change over pushbutton 161 is pushed, two selectable directions are displayed alternately by means of figures and letters in response to each pushing. At this time, if the tilt angle indicator 171 has been indicating nothing, "0" is displayed as the tilt angle. On the other hand, if some numerical value of the angle has been indicated, the prevailing state is continued.

OPERATION CAUSED BY TILT ANGLE INCREMENT/DECREMENT PUSHBUTTONS 172,173

As shown in FIG.5(C), as the tilt angle increment pushbutton 172 or decrement pushbutton 173 is pushed, in response thereto, the tilt angle displayed by indicator 171 is incremented or decremented. However, when nothing is displayed by the tilt angle indicator 171, i.e. when neither tilt angle is decided, manipulation of the pushbutton is ignored.

DISPLAY STATE OF CONTROL/DISPLAY PANEL AT TIME OF DETERMINING OF ONE SCAN PLANE

Figure 6:
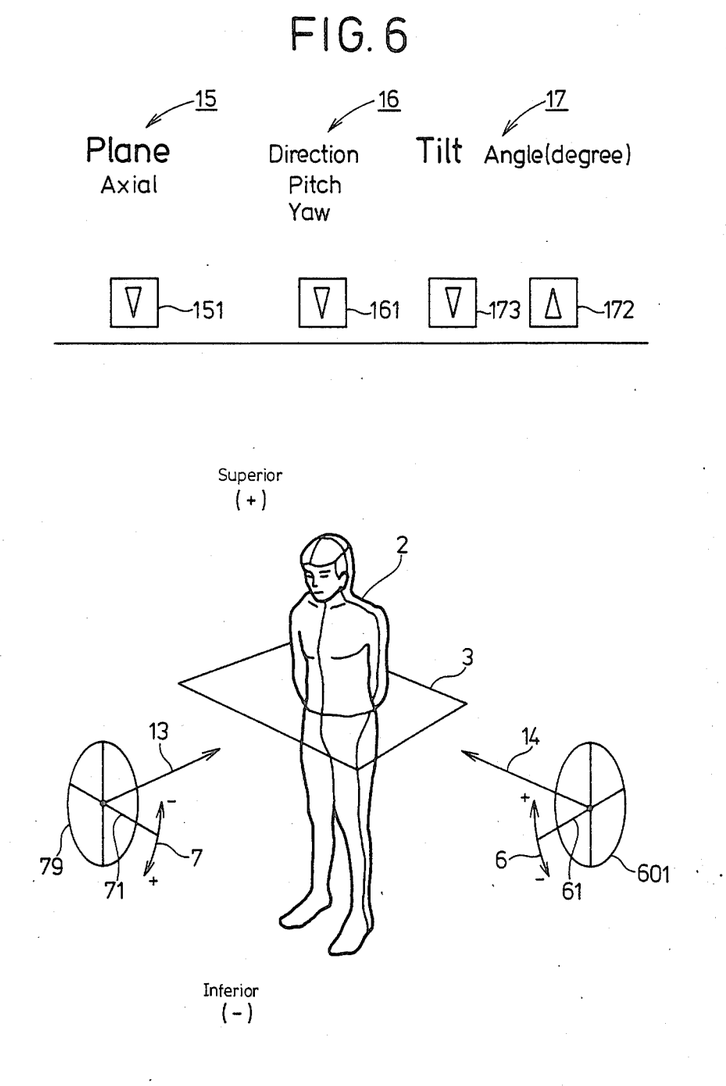
FIGS. 6,7,8 and 9 are pictorial views depicting display states of the control/display panel of the invention.
Figure 7:
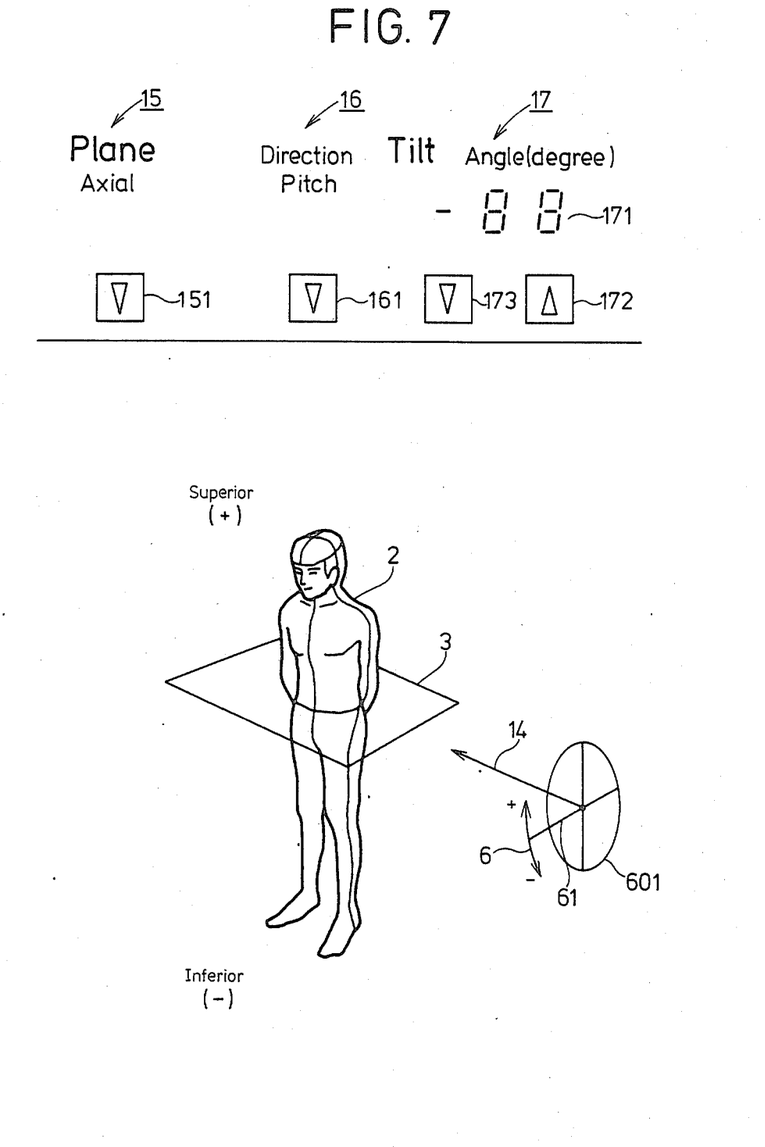

As shown in FIGS. 6,7, with reference to, for example, the Axial scan plane, the display state will be as follows. When the Axial plane is set by manipulation of plane change over pushbutton 151, LEDs $A_1$-$A_{10}$, AP, $LR_1$-$LR_6$, AY, $APo_1$-$APo_6$, Su, and in are energized. As a result, frame 3 is illuminated in superposed relation to body FIG. 2. Furthermore, there are turned on arrows 6,7 indicating the respective directions of Pitching and Yawing, straight lines 61,71, ellipses 601,79, arrows 13,14, indicating the respective directions of Anterior→Posterior, and Left→Right and the words "Superior" and "Interior". At the same time, the words "Axial", "Pitch" and "Yaw" are displayed, thereby resulting in the display state indicated in FIG. 6.

In the thus attained state, since "Pitching" is selected as the tilt direction by means of tilt direction change over pushbutton 161, the display "Yaw" disappears, while the display "Pitch" remains and the LEDs AY and $APo_1$-$APo_6$, among the LEDs in the energized state, are deenergized. As a result, arrow 7 indicating the direction of Yawing, straight line 71, ellipse 79, and arrow 13 indicating the direction of Anterior→Posterior disappear. On the other hand, there are left on arrow 6 indicating direction of Pitching, straight line 61, ellipse 601 and arrow 14, thereby resulting in the display state shown in FIG. 7.

Figure 8:
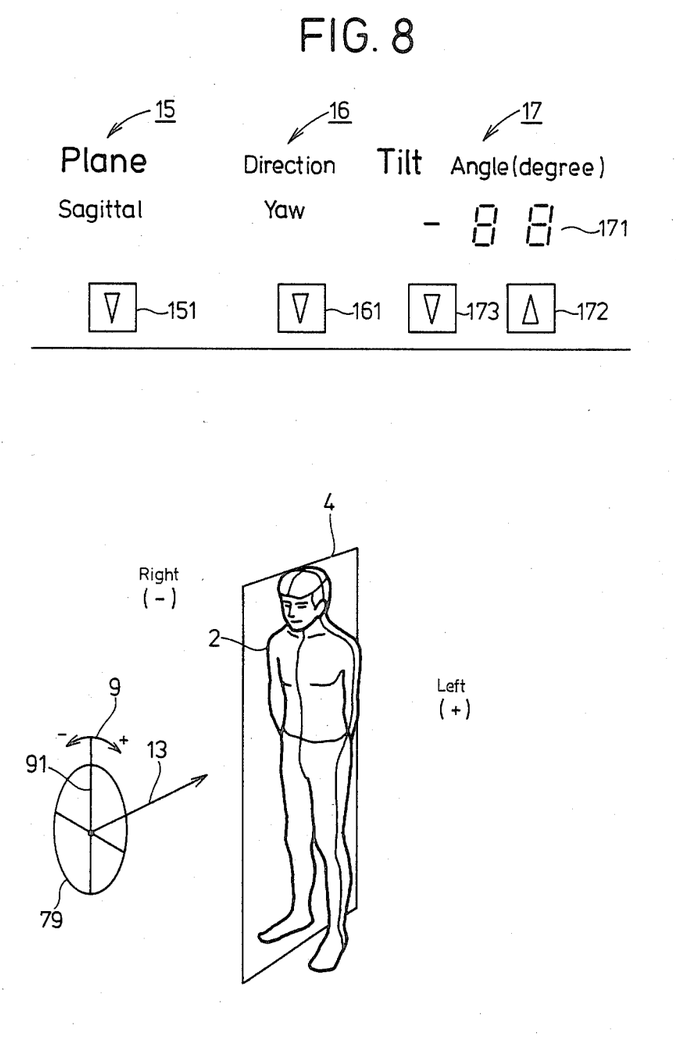
Figure 9:
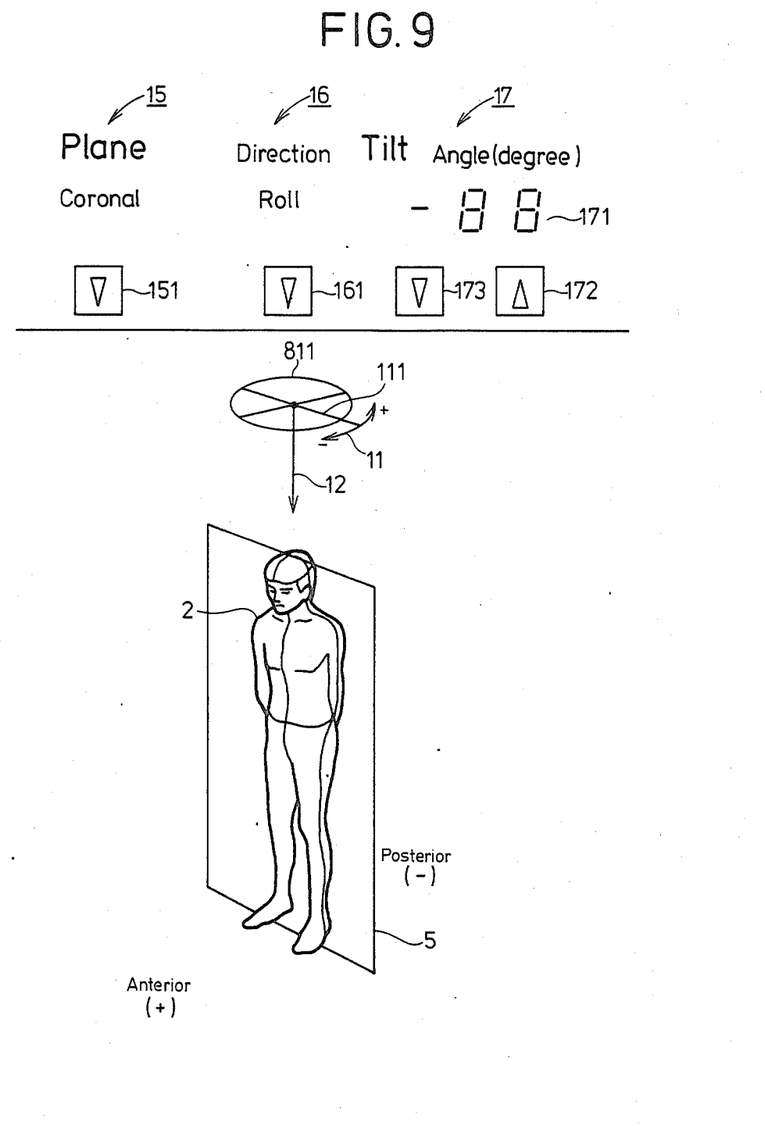

In the thus attained state, as the tilt angle increment pushbutton 172 or tilt angle decrement pushbutton 173 is pushed, the display value of the tilt angle indicator 171 changes so that the pitching angle is indicated. In FIGS. 7,8,9, the angles shown (i.e. −88) are illustrative. The actual tilt angle of the display state shown may be different.

Through observing the thus attained display state, it is possible for an unskilled operator to easily understand that the plane is axial and that the tilt direction is pitching from the body FIG. 2 with the related frame 3 indicating the axial plane, arrow 6 indicating the tilt direction and the ellipse 601 indicating the pitching. Of course, the tilt angle can be read out from the angle indicator 171.

In connection with the Sagittal plane and the Coronal plane, similarly to the above procedure, it is easy for the operator to perceive the scan plane and the tilt direction by means of the body FIG. 2 and the related frames 4,5, arrows 8,9,10,11, and ellipses 79,811.

FIG. 8 shows a display example when the Sagittal plane is subjected to Yawing. FIG. 9 shows a display example when the Coronal plane is subjected to Rolling. In either case, the scan plane and the tilt direction can be easily understood by the operator from the display, as discussed above.

Although the preferred embodiment was described, the invention should not be considered to be limited to such embodiment. For example in place of the control/display panel of the described configuration, the display section may comprise plasma display, CRT, fluorescent tube, liquid crystal, etc, to display the spatial arrangement of the scan plane with respect to the human body. Further, the invention may be used in a CT apparatus.

The foregoing description is illustrative of the principles of the invention. Numerous modifications and extensions thereof would be apparent to the worker skilled in the art. All such modifications and extensions are to be considered to be within the spirit and scope of the invention.

What is claimed is:

1. An operator console for use in an imaging diagnostic apparatus comprising
   body figure display means for displaying a frontal full length figure of a human body as viewed obliquely from above;
   axial plane display means for displaying a figure representing the axial plane of the body figure in superposed relation to the body figure;
   axial plane pitching display means for displaying a figure representing the pitching of the axial plane with respect to the figure representing the axial plane;
   axial plane yawing display means for displaying a figure representing the yawing of the axial plane with respect to the figure representing the axial plane;
   sagittal plane display means for displaying a figure representing the sagittal plane of the body figure in superposed relation to the body figure;
   sagittal plane rolling display means for displaying a figure representing the rolling of the figure representing the sagittal plane;
   sagittal plane yawing display means for displaying a figure representing the yawing of the figure representing the sagittal plane;
   coronal plane display means for displaying a figure representing the coronal plane of the body figure in superposed relation to the body figure;
   coronal plane pitching display means for displaying a figure representing the pitching of the coronal plane with respect to the figure representing the coronal plane;
   coronal plane rolling display means for displaying a figure representing the rolling of the coronal plane with respect to the figure representing the coronal plane;
   plane designating means manipulatable by an operator to output a signal for designating a plane;
   plane display control means for validating the display operation of one among the axial plane display means, sagittal plane display means, and coronal plane display means on the basis of the output signal of the plane designating means;

tilt direction designating means manipulatable by an operator to output a tilt direction designating signal; and tilt direction display control means for validating the display operation of one among the axial plane pitching display means, axial plane yawing display means, sagittal plane rolling display means, sagittal plane yawing display means, coronal plane pitching display means, and coronal plane rolling display means on the basis of the output signal of the tilt direction designating means and the output signal of the plane designating means.

* * * * *